United States Patent [19]

Tóth et al.

[11] Patent Number: 4,696,899
[45] Date of Patent: Sep. 29, 1987

[54] PROCESS FOR THE PREPARATION OF HUMAN LEUKOCYTE AND HUMAN GAMMA INTERFERON

[75] Inventors: Miklós Tóth, Szeged; Valéria Endrész, Adony; Ilona Béládi; Sándor Tóth, both of Szeged, all of Hungary

[73] Assignee: EGYT Gyogyszervegyeszeti Gyar, Budapest, Hungary

[21] Appl. No.: 681,451

[22] Filed: Dec. 10, 1984

[30] Foreign Application Priority Data

Dec. 13, 1983 [HU] Hungary ................. 4237-83

[51] Int. Cl.$^4$ ............... C12P 21/00; A61K 45/02
[52] U.S. Cl. ...................... 435/68; 424/85; 435/811; 530/351
[58] Field of Search ............ 435/68, 240; 424/85; 530/351

[56] References Cited

U.S. PATENT DOCUMENTS 4,296,025 10/1981 Sugimoto ............. 424/85

FOREIGN PATENT DOCUMENTS 3136166 4/1983 Fed. Rep. of Germany .
83/01899 6/1983 PCT Int'l Appl. .

OTHER PUBLICATIONS

Wiranowska-Stewart, J. Interferon Research, vol. 1, pp. 315-321, 1981.

Cantell et al., Proc. of Tissue Culture Association Workshop, Lake Placid, New York, pp. 35-38, 1973.
Torna et al., J. Biol. Chem., vol. 251, pp. 4810-4816, 1976.

Primary Examiner—Blondel Hazel
Attorney, Agent, or Firm—Gabriel P. Katona

[57] ABSTRACT

The invention relates to a process for the preparation of $\alpha$- and $\gamma$-interferon by isolating the buffy coat fraction of blood, removing the erythrocytes, suspending the leukocytes in a suitable nutrient medium and treating with an $\alpha$-interferon inducer and with a $\gamma$-interferon inducer, which comprises producing $\alpha$-interferon and $\gamma$-interferon one after the other in the same leukocyte culture by pre-treating the suspension obtained after the separation of the leukocyte/buffy coat/fraction of blood, removal of the erythrocytes and suspending the leukocytes in a suitable nutrient medium with - or $\beta$-interferon, contacting with an $\alpha$-interferon inducer, separating the liquid containing the $\alpha$-interferon from the cells, if desired recovering the -interferon, washing and suspending the cells in a suitable nutrient medium, treating with a mitogenic agent, separating the liquid comprising $\alpha$-interferon from the cells and if desired recovering $\alpha$-interferon and if desired making $\alpha$-interferon free of $\alpha$-interferon.

The advantage of the process is that $\alpha$- and $\gamma$-interferon are produced from the same leukocyte culture in two steps. This makes the process more economical and enables an effective utilization of the limitedly available leukocytes.

20 Claims, 1 Drawing Figure

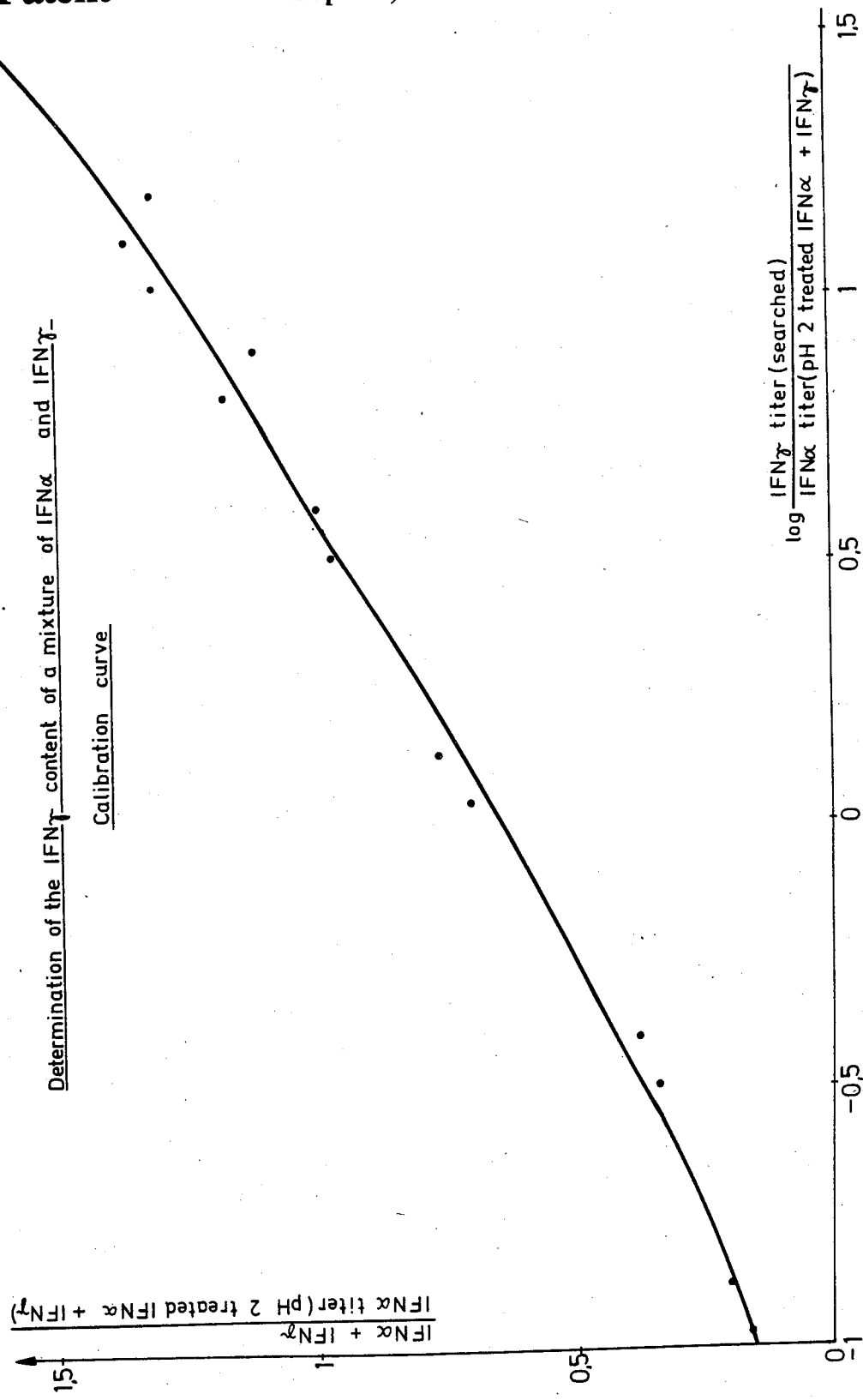

PROCESS FOR THE PREPARATION OF HUMAN LEUKOCYTE AND HUMAN GAMMA INTERFERON

This invention relates to a process for the preparation of human leukocyte and human gamma interferon.

According to the present invention there is provided a process for the preparation of α- and γ-interferon from the same cell population in two steps. Thus our invention enables the maximal and optimal utilization of the interferon producing capacity of human leukocytes being available but in a limited amount.

It is known that from human leukocytes α-interferon can be produced by means of a virus and γ-interferon with the aid of mitogenic agents. The production of the said two types of interferon is limited by the fact that human leukocytes are but limitedly available. Human therapy needs both types of interferon because the different interferon types possess different advantageous properties (thus α-interferon exhibits particularly antiviral and γ-interferon antitumour activity) and a combined application of interferons is desirable as different interferons potentiate the activity of each other (antiviral, antitumour, immunomodulant effects). Since both types of interferon are produced from leukocytes available but in a limited amount the preparation of one interferon type excludes the production of the other.

It is the object of the present invention to elaborate a process for the preparation of α- and γ-interferon from one and the same leukocyte culture. Numerous attempts were made to produce from the same cell population α-interferon several times. These attempts failed to succeed however because the large amount of α-interferon produced by the cells retroacts on the cells which get into a hyporeactive state and consequently in the next induction step the α-interferon producing capacity of the cells diminishes drastically.

The present invention is based on the recognition that even on treating a γ-interferon producing system with a large amount of α-interferon the system does not get into a hyporeactive state, on the other hand more interferon is produced than in the untreated sample. This also happens at the end of α-interferon producing period, whereby a large amount of α-interferon is obtained and at the same time the interferon producing ability of the γ-interferon producing cells is maintained, moreover increased.

According to the present invention there is provided a process for the preparation of α- and γ-interferon by isolating the buffy coat fraction of blood, removing the erythrocytes, suspending the leukocytes in a suitable nutrient medium and treating with an α-interferon inducer and with a γ-interferon inducer, which comprises producing α-interferon and γ-interferon one after the other in the same leukocyte culture by pre-treating the suspension obtained after the separation of the leukocyte (buffy coat) fraction of blood, removal of the erythrocytes and suspending the leukocytes in a suitable nutrient medium with α- or β-interferon, contacting with an α-interferon inducer, separating the liquid containing the α-interferon from the cells, if desired recovering the α-interferon, washing and suspending the cells in a suitable nutrient medium, treating with a mitogenic agent, separating the liquid comprising γ-interferon from the cells and if desired recovering γ-interferon and if desired making γ-interferon free of α-interferon.

According to the process of the present invention as starting material the buffy coat fraction (leukocytes) of anticoagulated human blood stored at 0°-8° C. for not more than 48 hours is used.

As anticoagulant an ACD solution (a solution comprising citric acid and dextrose) or an ACD solution supplemented by various bases (e.g. adenine or guanine) can be used. The collected leukocytes may be removed by gradient-centrifuging (e.g. Ficoll or Percoll) or preferably by haemolysis carried out with ammonium chloride.

One may proceed by preferably admixing the concentrated leukocyte suspension with a 0.5-1.0%—preferably 0.83%—ammonium chloride solution having a temperature of 0°-10° C. in a volume ratio of 1:3-20, preferably 1:5. The suspension is incubated at 0°-8° C. for 5-20 minutes—preferably for 10 minutes—with or without stirring. The leukocytes are separated from the disintegrated erythrocytes (e.g. by centrifuging). One may proceed preferably by repeating the ammonium chloride treatment by using 10 parts by weight of an ammonium chloride solution related to 1 part by volume of a cell suspension.

The purified leukocytes are incubated in a nutrient solution of a cell culture comprising amino acids and vitamines (e.g. an Eagle nutrient medium, RPMI 1640, Dulbecce modified MEM, Glasgow modified MEM etc.). It is also preferred to use a cheap nutrient medium of the following composition which can be autoclavized.

| Component | Amount mg/l |
|---|---|
| Calcium chloride | 175-350 |
| Potassium chloride | 300-500 |
| Magnesium sulfate or magnesium chloride | 175-500 |
| Sodium chloride | 5,000-7,000 |
| Sodium hydrogen carbonate | 200-3,500 |
| Sodium dihydrogen phosphate | 30-150 |
| Glucose | 500-5,500 |
| Ferric nitrate | 0-0.2 |

The cell number is adjusted to $10^6$–$10^8$, preferably $10^7$ cells/ml.

The nutrient medium used is supplemented with an animal or human serum or gamma globulin free serum (0.5-10%). It is preferred to add an antibiotic (e.g. neomycin or gentamycin) to the nutrient medium.

The cells are then reated with α- or β-interferon. For this purpose inducer free crude or purified interferon may be used in an amount of 10-500 IU/ml, preferably 200-300 IU/ml. The pre-treatment is carried out at 35°-39° C.—preferably at 37° C.—for 1-6 hours—preferably for 2 hours.

The cells are then contacted with an α-interferon inducer, preferably crude or purified Sendai virus which is advantageously applied in a concentration of 100-800—preferably 400—hemagglutinizing units/ml.

Induction is carried out for 5-48 hours—preferably for 15-20 hours—at a temperature between 35°-39° C.—preferably at 37° C. The cells are thereafter separated from the liquid phase. The supernatant comprises the crude α-interferon which may be stored at a temperature between −20° C. and +4° C. or purified by known methods.

The cells are then washed, preferably once with a physiological salt solution, particularly with a nutrient medium having the above composition. After washing the cell concentration is adjusted to the value of $5 \times 10^6$–$10^8$, preferably to $2.5 \times 10^7$ in a nutrient medium, preferably in a nutrient medium having the composition disclosed above. The nutrient medium comprises a human or animal serum or globulin-free serum, preferably human globulin-free serum, in a concentration of 0.5–5 mg/ml, preferably 1–2 mg/ml (3–6%).

The cells are then contacted with a $\gamma$-interferon inducer. For this purpose preferably Concanavalin A, Phytohamagglutinin or Staphylococcus enterotoxin may be used. It is preferred to use Concanavalin A as inducer, advantageously in a concentration of 2.5–30 $\mu$g/ml, particularly 15 $\mu$g/ml.

Induction is generally carried out for 8–48 hours—preferably for 12–16 hours—at a temperature of 35°–39° C.—preferably 37° C. The inducer may be removed if desired after a certain period of time (e.g. 1 hour) by washing but this step may also be omitted, because the presence of the inducer does not effect interferon production in an adverse manner. For this reason the inducer is not removed generally. The cells are then separated from the liquid phase. The supernatant comprises crude $\gamma$-interferon which is contaminated by $\alpha$-interferon since in the second period of interferon production (i.e. in the period of $\gamma$-interferon production) the $\alpha$-interferon producing cells also produce some interferon.

Since the interferons potentiate the antiviral activity of each other, the actual $\gamma$-interferon content of the mixture of $\alpha$- and $\gamma$-interferons can only be calculated by means of a calibration curve (FIG. 1). In order to calculate the amount of $\gamma$-interferon it is necessary to know the potentiated titer and $\alpha$-interferon content of the mixture. The latter value can be determined by treating the mixture at pH 2 and thereafter titrating the same, since the $\gamma$-interferon can be selectively decomposed at this pH value.

Pure $\gamma$-interferon is obtained by removing the $\alpha$-interferon content of crude $\gamma$-interferon. The crude $\gamma$-interferon is partially purified and concentrated (e.g. on CPG-350 porous glass particles, Electro-Nucleonic N.J. U.S.A.) preferably before the removal of $\alpha$-interferon. The following methods may be used: one method is based on the different molecular weight of the two types of interferon ($\alpha$ = 18,000–21,000 daltons; $\gamma$ = 40,000–45,000 daltons) and is carried out by gel filtration (e.g. Sephacryl S-200 chromatography). According to the other method $\alpha$-interferon which contaminates $\gamma$-interferon is bound by anti-d-interferon antibodies attached to Sepharose gel.

The advantage of the process of the present invention is that $\alpha$- and $\gamma$-interferon can be produced in the same leukocyte culture in two steps. The costs of production of 1 interferon unit significantly decrease because the larger part of the manufacturing costs of interferon consists of the collection of blood samples, preparation of the "buffy coat" fraction and purification of the leukocytes. The process of the present invention enables the significant increase of the interferon production of the but limitedly available leukocytes.

Further details of the present invention are to be found in the following Examples without limiting the scope of invention of said Examples.

EXAMPLE 1

Blood samples are stored in an ACD solution (aqueous solution comprising citric acid and dextrose) at +4° C. for 3 hours. 1 part by volume of the leukocyte concentrate thus obtained is admixed with 5 parts by weight of 0.83% icecold aqueous ammonium chloride solution. The suspension is allowed to stand in ice until lysis of the erythrocytes takes place (5–10 minutes) whereupon the leukocytes are suspended in a nutrient medium having the following composition:

| Component | Amount, mg/l |
| --- | --- |
| Calcium chloride | 175–350 |
| Potassium chloride | 300–350 |
| Magnesium sulfate or magnesium chloride | 175–500 |
| Sodium chloride | 5,000–7,000 |
| Sodium hydrogen carbonate | 200–3,500 |
| Sodium dihydrogen phosphate | 30–150 |
| Glucose | 500–5,500 |
| Ferric nitrate | 0–0.2 mg/l |

The above operation of the lysis of erythrocytes is repeated with the difference that 10 parts by volume of 0.83% aqueous ammonium chloride solution are used related to 1 part of leukocyte suspension. The leukocytes are suspended in the nutrient medium of the above composition and the cell number is adjusted to the value of $1 \times 10^7$ cells/ml.

The nutrient medium contains 2 mg/ml of human globulin-free serum (about 6%). The cells are treated with 200 IU/ml of an inducer-free concentrated human $\alpha$-interferon at 37° C. under constant stirring. After two hours the cells are induced with 400 hemagglutinizing units of Sendai virus. Incubation is terminated in the eighteenth hour after induction. The antiviral $\alpha$-interferon titer of the supernatant amounts to 54,200 IU/ml. The cells used for the production of $\alpha$-interferon are washed once with the above nutrient medium and the leukocytes are suspended in the nutrient medium in a concentration of $2.5 + 10^7$ cells/ml. The nutrient medium contains 1 mg/ml of globulin-free human serum (about 3%). The cells are then stimulated with 15 $\mu$g/ml of Concanavalin A. The inducer is not removed from the system. Incubation is carried out at 37° C. under constant stirring and the supernatant is removed from the cells by centrifuging in the sixteenth hour after induction. The antiviral titer of the supernatant comprising the $\gamma$-interferon is determined on a WISH human animal cell and the titers are expressed in U/ml (units/ml) after comparing the same to human $\alpha$-interferon standard (for the time being there is no international human $\gamma$-interferon standard composition). The titer of the supernatant amounts to 10,600 U/ml which is however of a potentiated level because the $\gamma$-interferon compositions prepared comprise $\alpha$-interferon too. With the aid of the calibration curve of FIG. 1 and on the basis of the titer of the original substance and that treated at pH 2 the actual $\gamma$-interferon content amounts to 1,840 u/ml.

For the sake of comparison the above process is repeated except that before $\gamma$-interferon production the cells are incubated without Sendai virus for a day.

The $\gamma$-interferon titer produced by Concanavalin A amounts to 340 U/ml.

For the sake of comparison isolated leukocytes are immediately induced with Concanavalin A under omitting the first—i.e. $\alpha$-interferon producing—period. The titer of the produced $\gamma$-interferon amounts to 450 U/ml.

If the $\alpha$-interferon producing period is omitted and the leukocytes are treated with 1,500 IU/ml human $\alpha$- or $\beta$-interferon prior to induction for 4 hours (priming), the titer of γ-interferon produced amouts to 2,300 U/ml.

EXAMPLE 2

One proceeds according to Example 1 except that as nutrient medium an Eagle-solution is used [Virology 14, 359 (1961)]. The titer of α-interferon amounts to 56,000 IU/ml. In the second phase of the production the γ-interferon titer in the same nutrient medium amounts to 1,680 U/ml.

If the α-interferon production is omitted, the titer of γ-interferon produced amounts to 280 U/ml.

What we claim is:

1. A process for the preparation of alpha-interferon and gamma-interferon one after the other in the same leukocyte culture, which comprises:
   (a) isolating the buffy coat fraction of blood,
   (b) removing the erythrocytes,
   (c) suspending the leukocytes in a suitable nutrient medium,
   (d) pretreating said suspension with alpha- or beta-interferon,
   (e) then contacting it with an alpha-interferon inducer,
   (f) separating the liquid containing the alpha-interferon from the cells,
   (g) washing and suspending the cells in a suitable nutrient medium,
   (h) treating said cells with a mitogenic agent,
   (i) separating the liquid containing gamma-interferon and alpha-interferon from the cells, and
   (j) finally recovering gama-interferon from the mixture.

2. Process according to claim 1, which comprises carrying out pre-treatment with 10–500 IU/ml of α- or β-interferon.

3. Process according to claim 1, which comprises carrying out pre-treatment for 1–6 hours 4. Process according to claim 1, which comprises carrying out pre-treatment at 35°–39° C.

5. Process according to claim 1, which comprises using crude or purified Sendai virus as α-interferon inducer.

6. Process according to claim 5, which comprises using Sendai virus in a concentration of 100–800 hemagglutinizing units per ml.

7. Process according to claim 5, which comprises carrying out α-interferon induction for 5–48 hours.

8. Process according to claim 5, which comprises carrying out α-interferon induction at 35°–39° C.

9. Process according to claim 1, which comprises using Concanavalin A, Phytohaemagglutinin or staphylococcus enterotoxin as mitogenic agent.

10. Process according to claim 9, which comprises carrying out γ-interferon induction for 8–48 hours.

11. Process according to claim 1, which comprises partially purifying and concentrating the crude γ-interferon obtained and removing the α-interferon content thereof by gel filtration or binding the α-interferon with anti-α-interferon antibodies.

12. Process according to claim 1, which comprises removing the erythrocytes from the buffy coat fraction by means of haemolysis with ammonium chloride.

13. Process according to claim 1, which comprises using as nutrient medium an aqueous solution comprising 175–350 mg/l of calcium chloride, 300–500 mg/l of potassium chloride, 175–500 mg/l of magnesium sulfate or an equivalent amount of magnesium chloride, 5,000–7,000 mg/l of sodium chloride, 200–3,500 mg/l of sodium hydrogen carbonate, 30–150 mg/l of sodium dihydrogen phosphate, 500–5,500 mg/l of glucose and with or without 0.0–0.2 mg/l of ferric nitrate and 0.5–10% of serum or serum protein (0.5–5 mg/ml.).

14. The process of claim 2, wherein the pretreatment is carried out with 200–300 IU/ml of alpha- or beta-interferon.

15. The process of claim 3, wherein the pretreatment is carried out for about 2 hours.

16. The process of claim 4, wherein the pretreatment is carried out at about 37 degrees centigrade.

17. The process of claim 6, wherein Sendai virus is used in a concentration of about 400 hemagglutinizing units per ml.

18. The process of claim 7, wherein alpha-interferon induction is carried out for about 15–20 hours.

19. The process of claim 8, wherein alpha-interferon induction is carried out at about 37 degrees centigrade.

20. The process of claim 10, wherein gamma-interferon induction is carried out for about 12–26 hours.

* * * * *